US011401252B2

(12) United States Patent
Jemaa et al.

(10) Patent No.: US 11,401,252 B2
(45) Date of Patent: Aug. 2, 2022

(54) LIGNIN RECOVERY AND FURFURAL PRODUCTION FROM PREHYDROLYSATE STREAMS

(71) Applicant: FPInnovations, Pointe-Claire (CA)

(72) Inventors: Naceur Jemaa, Pointe-Claire (CA); Adil Mazar, Montréal (CA); Waleed Wafa Al Dajani, Pierrefonds (CA); Michael Paleologou, Beaconsfield (CA)

(73) Assignee: FPInnovations, Pointe-Claire (CA)

( * ) Notice: Subject to any disclaimer, the term of this patent is extended or adjusted under 35 U.S.C. 154(b) by 715 days.

(21) Appl. No.: 16/088,980

(22) PCT Filed: Apr. 20, 2017

(86) PCT No.: PCT/CA2017/050486
§ 371 (c)(1),
(2) Date: Sep. 27, 2018

(87) PCT Pub. No.: WO2017/181280
PCT Pub. Date: Oct. 26, 2017

(65) Prior Publication Data
US 2020/0325111 A1 Oct. 15, 2020

Related U.S. Application Data

(60) Provisional application No. 62/324,990, filed on Apr. 20, 2016.

(51) Int. Cl.
*C07D 307/50* (2006.01)
(52) U.S. Cl.
CPC ................... *C07D 307/50* (2013.01)

(58) Field of Classification Search
CPC ..................................................... C07D 307/50
USPC ......................................................... 424/489
See application file for complete search history.

(56) References Cited

FOREIGN PATENT DOCUMENTS

DE            3139188         7/1983

OTHER PUBLICATIONS

Montané et al. "High-temperature dilute-acid hydrolysis of olive stones for furfural production", Biomass and Bioenergy, vol. 22, No. 4, pp. 295-304.
Baktash et al. "Production of furfural from an industrial pre-hydrolysis liquor", Separation and Purification Technology, vol. 149, pp. 407-412.

*Primary Examiner* — Taylor V Oh
(74) *Attorney, Agent, or Firm* — Norton Rose Fulbright Canada LLP (57) ABSTRACT

The present invention relates to a method of producing furfural and extracting lignin from a hemi-cellulosic biomass solution comprising a total quantity of C5 sugars, comprising the steps of heating the hemi-cellulosic biomass solution to a temperature of at least about 200° C.; acidifying the hemi-cellulosic biomass solution with acid to produce the furfural in vapor phase; and condensing the furfural to recover furfural in solution, wherein the furfural is produced at a total molar yield of at least 70% of moles of furfural produced/the total moles C5 sugars present in the initial hemi-cellulosic biomass solution. Low molecular weight lignin can also be recovered from the hemi-cellulosic biomass solution prior to furfural production by membrane concentration, acidification, coagulation and filtration.

19 Claims, 4 Drawing Sheets

LIGNIN RECOVERY AND FURFURAL PRODUCTION FROM PREHYDROLYSATE STREAMS

CROSS-REFERENCE TO RELATED APPLICATIONS

This application is a U.S. National Phase of International Application No. PCT/CA2017/050486, filed on Apr. 20, 2017 and claiming priority from U.S. provisional patent application 62/324,990 filed on Apr. 20, 2016, and this application claims priority to and the benefit of the above-identified applications, each of which are incorporated by reference herewith in their entirety.

TECHNICAL FIELD

It is provided a method of producing furfural and extracting lignin from a hemi-cellulosic biomass solution.

BACKGROUND ART

Several processes have been described to derive chemicals/fuels from biomass. These processes employ chemicals or enzymes or a combination of the two with the objective of releasing part or all the sugars present in the biomass. For example, extraction of hemicellulose prior to a pulping process can be achieved biologically (with enzymes) and chemically (i.e. cold/hot water, steam, concentrated/dilute acid hydrolysis, sodium/potassium hydroxide). Hot water or steam prehydrolysis is practiced prior to pulp production during the production of kraft dissolving pulp using hardwood chips. The same approach can be implemented in sulfite or mechanical pulping processes. It is thus commonly known that hot water can be used in a prehydrolysis step to extract sugars. Further, sodium carbonate-based chemical pulping processes are used in a few pulp mills. Such processes remove a portion of the lignin and hemicellulose from the wood chips without the latter being oxidized to saccharinic acids as is the case with more alkaline pulping processes.

During a typical hydrolysis step, the hemicellulose polymer yields a mixtures of monosaccharide wood sugars, oligomeric wood sugars, and other products, predominantly furfural, hydroxymethylfurfural, and levulinic acid (from dehydration of sugars), acetic acid (from deacetylation of acetylated hemicelluloses), and phenolic compounds (from lignin). For hardwoods, the predominant sugars are pentoses such as xylose and xylooligomers. For softwoods, hexoses such as mannose, galactose and glucose are the major constituents.

Furfural, an important chemical solvent, is an organic compound derived from a variety of agricultural byproducts such as corncobs, oat hulls, cottonseed hull bran, cottonseed hulls, rice hulls, bagasse, and sawdust. Furfural is a heterocyclic aldehyde ($C_5H_4O_2$). Furfural represents an important renewable, non-petroleum based chemical feedstock. Furfuryl alcohol represents the major market for furfural. Production of furfuryl alcohol after hydrogenation of furfural can be used to produce tetrahydrofurfuryl alcohol which is a common nonhazardous solvent in agricultural formulations and an adjuvant to help herbicides penetrate leaf structures. Furfural is also used to make other chemical and pharmaceutical intermediates such as tetrahydrofuran (THF) and furan polymers.

The furfural yield in known extraction processes does not exceed generally 50% due to side reactions that take place at high furfural levels and high residence times. To reduce these side reactions, biphasic reactors have been proposed. In this approach, an organic phase or a solvent such as butanol is employed to extract the furfural as it is produced to avoid its degradation. However, this approach introduces new steps and increases the capital and operating costs. In addition, high solvent recovery rates are needed to make the process economically viable.

Several processes have been devised to produce furfural from different agricultural feedstocks and pentosan-rich aqueous streams. Producing furfural from solid biomass is associated with several challenges as it requires a significant amount of acid catalysts to hydrolyze the sugars first before their conversion to furfural. In addition, a good metallurgy of the reactor (and other equipment) is needed. Several catalysts such as mineral, organic, and solid acids have been proposed to increase the furfural yield. The use of organic phases to separate the furfural while it is produced has been suggested as well. U.S. Pat. No. 8,524,924 describes the production of furfural from lignocellulosic feedstocks such as corn cob, wheat straw, sawdust, and bagasse. Sulfuric acid (at 3.75 wt %) was employed as a catalyst. A water-immiscible organic phase such as toluene and methyl isobutyl ketone (MBIK) was employed to extract the furfural. In such an approach, the recovery of the solvent is critical and has a significant impact on the economic viability of the process. As described in Mao et al. (2013, Green Chem, 15: 727-737), acetic acid can be used to catalyze furfural production from biomass. Acetic acid can be used to break down the biomass, release sugars and catalyze their conversion to furfural. High quantities of acetic acid need to be used and, unfortunately, this process is associated with a low yield in the recovery of furfural. Organic acids have also been used as cooking chemicals (high concentration of acids at high temperatures such as 90-180° C.) in pulp production processes (see U.S. 2004/0040830 and WO 03/074781). However, several side reactions involving, for example, furfural are observed in such processes, leading to a low yield of furfural. Zeitsch proposed the use of phosphoric acid to avoid the side reactions in K. J. Zeitsh, "The Chemistry and technology of Furfural and its Many By-Products"; Elsevier: London, 2000, p. 61. However, phosphoric acid is very expensive compared to sulphuric acid and presents environmental issues. U.S. Pat. No. 8,524,925 proposes the use of metal halides such as NaCl as a catalyst in combination with a solvent. Sodium chloride solutions are corrosive and are not preferred over other catalysts.

Prehydrolysate liquor from a dissolving pulp mill was employed by Liu et al. (2015, Journal of Wood Chemistry and Technology, 35: 260-269). Acetic acid was used as a catalyst, however, the furfural yield was only about 41.5%.

The recovery of lignin from sugar-rich streams prior to furfural production was rarely considered in the prior art. Shen et. al. (2013, Bioresource Technology, 127: 59-65) proposed the use of activated carbon to remove lignin from the prehydrolysatre liquor. By doing so, the lignin cannot be recovered and is wasted with the activated carbon.

It is thus still desirable to be provided with a mean to produce furfural at high yield and to extract it efficiently from C5-rich streams. It will be beneficial to use minimum amounts of cheap catalysts such as sulfuric acid. It will be beneficial also to provide a method for the recovery of lignin.

SUMMARY

In accordance with the present disclosure, there is now provided a method of producing furfural comprising providing a hemi-cellulosic biomass solution comprising a total quantity of C5 sugars; heating the hemi-cellulosic biomass solution to a temperature of at least about 200° C.; acidifying the hemi-cellulosic biomass solution with acid to produce the furfural in vapor phase; and condensing the furfural to recover furfural in solution, wherein the furfural is produced at a total yield of at least 70% moles of furfural produced/the total moles of C5 sugars present in the initial hemi-cellulosic biomass solution.

In accordance with the present disclosure, there is also provided a method of producing furfural comprising providing a hemi-cellulosic biomass solution comprising a total quantity of C5 sugars; passing the hemi-cellulosic biomass solution through a 1000 Da cut-off membrane to separate the lignin from the hemi-cellulosic biomass solution; acidifying the concentrated hemi-cellulosic biomass solution to pH 2; coagulating the lignin particles forming a lignin cake; separating the lignin cake by filtration; heating the filtered hemi-cellulosic biomass solution at atmospheric pressure or less, to a temperature of at least about 200° C.; acidifying the hemi-cellulosic biomass solution with acid to produce the furfural in vapour phase; and condensing the furfural to recover furfural in solution, wherein the furfural is produced at a total molar yield of at least 76% of moles of furfural produced/the total moles C5 sugars present in the initial hemi-cellulosic biomass solution.

In an embodiment, the total molar yield is at least 75%.

In another embodiment, the acid used to acidify the hemi-cellulosic biomass solution is sulfuric acid.

In a further embodiment, the sulfuric acid has a concentration of 0.1%-0.5% w/w of the hemi-cellulosic biomass solution.

In a supplemental embodiment, the sulfuric acid has a concentration of 0.25% w/w of the hemi-cellulosic biomass solution.

In an embodiment, the temperature to which the hemi-cellulosic biomass solution is heated is between 220° C.-240° C.

In another embodiment, the temperature to which the hemi-cellulosic biomass solution is heated to 240° C.

In an embodiment, the method described herein further comprises the step of purifying and concentrating the furfural by distillation.

In another embodiment, the furfural is separated from water and acetic acid by distillation.

In an embodiment, the hemi-cellulosic biomass solution is from hardwood chips, hardwood (HW) lignin plant; black liquor from HW pulp mills; red liquor from hardwood sulfite pulp mills; C5 sugar streams from thermo-mechanical pulping bio-plants; C5-rich sugar stream from CNC production; and non-wood sources.

In an additional embodiment, the non-wood sources are oats and annual plants.

In a further embodiment, the hemi-cellulosic biomass solution is a prehydrolysate stream.

In an embodiment, the prehydrolysate stream is obtained by contacting the hemi-cellulosic biomass with steam, hot water, a mild acidic stream, an alkaline solution, or a solvent.

In another embodiment, the furfural is produced at a total molar yield of at least 75.7% moles of furfural produced/the total moles C5 sugars present in the initial hemi-cellulosic biomass solution.

In an additional embodiment, the furfural is produced at a total molar yield of at least 80% of moles of furfural produced/the total moles C5 sugars present in the initial hemi-cellulosic biomass solution.

In a further embodiment, the furfural is produced at a total molar yield of at least 85% of moles of furfural produced/the total moles C5 sugars present in the initial hemi-cellulosic biomass solution.

In an embodiment, the method described herein further comprises a first step of extracting lignin from the provided hemi-cellulosic biomass solution by concentration using membranes.

In an embodiment, the membrane cut-off is a 1000 Da.

In another embodiment, acetic acid is recovered from the permeate from the 1000 Da cut-off membrane using a hollow fiber contactor.

In another embodiment, the hemi-cellulosic biomass solution is acidified to pH 2 after being concentrated with the 1000 Da cut-off membrane.

BRIEF DESCRIPTION OF THE DRAWINGS

Reference will now be made to the accompanying drawings.

It will be noted that throughout the appended drawings, like features are identified by like reference numerals.

DETAILED DESCRIPTION

It is provided a method of making furfural from biomass.

Figure 1A:
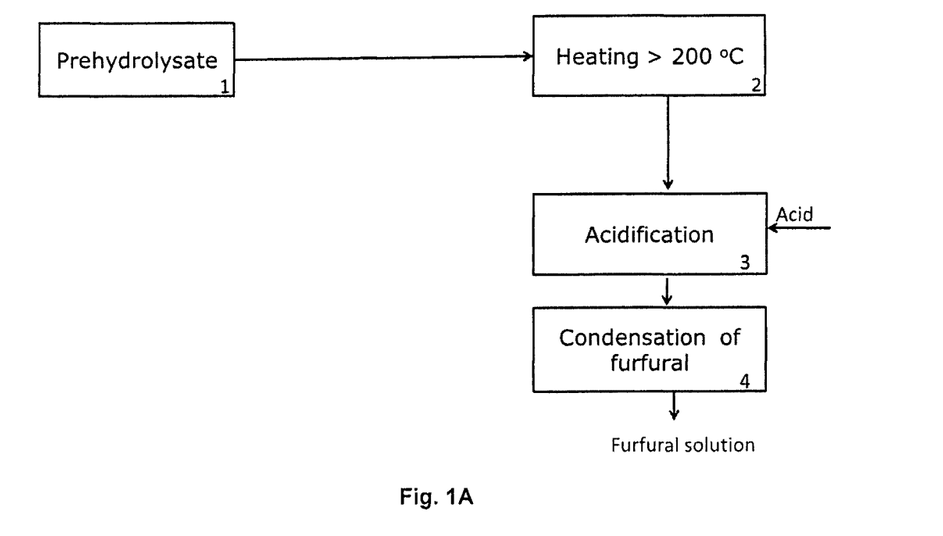
FIG. 1a illustrates schematically a process of producing furfural according to an embodiment described herein.

As described herein and as illustrated in FIG. 1a, it is disclosed a method comprising the steps of providing a hemi-cellulosic biomass solution 1 comprising a total quantity of C5 sugars; heating 2 the hemi-cellulosic biomass solution (prehydrolysate) to a temperature of at least about 200° C.; acidifying 3 the hemi-cellulosic biomass solution with acid to produce the furfural in vapour phase; and condensing 4 the furfural to recover furfural in solution.

Figure 1B:
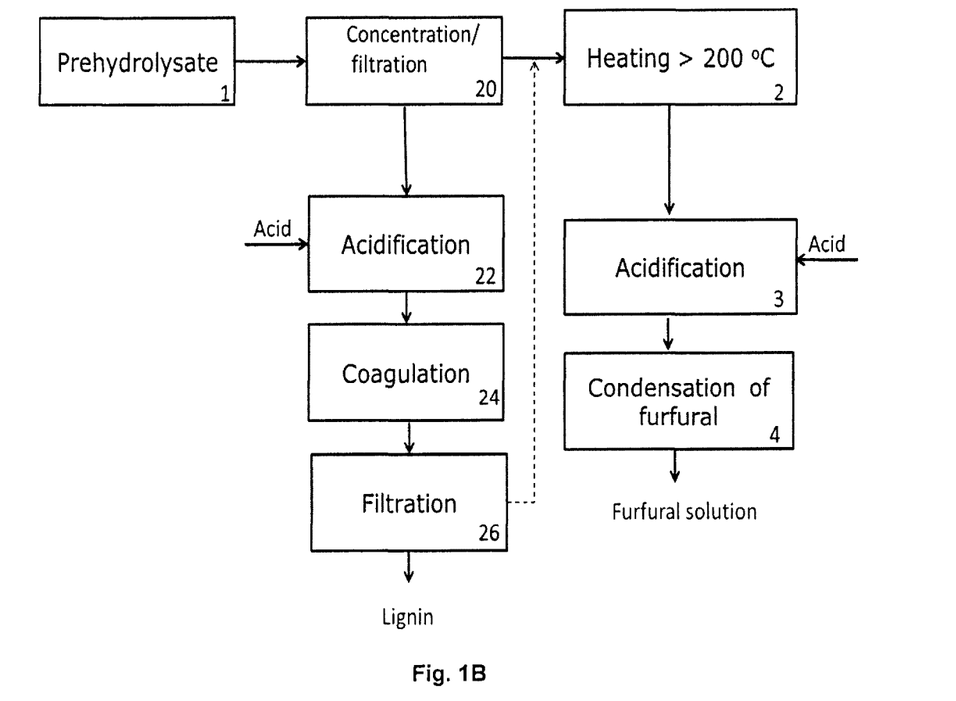
FIG. 1b illustrates schematically a process of producing furfural and extracting lignin according to another embodiment described herein.

In FIG. 1b, the hemi-cellulosic biomass solution 1 is concentrated using a membrane filtration unit 20 until a desirable solid content of about 20% is reached. The concentrate from 20 is acidified 22 by the addition of an acid to about pH=2. The solution is left to allow the lignin particles to coagulate 24 at about 73° C. Filtration 26 is then performed to separate the lignin from the liquor. The liquor can be mixed with the permeate of the filtration unit 20 to increase the sugar recovery and furfural production.

Figure 2:
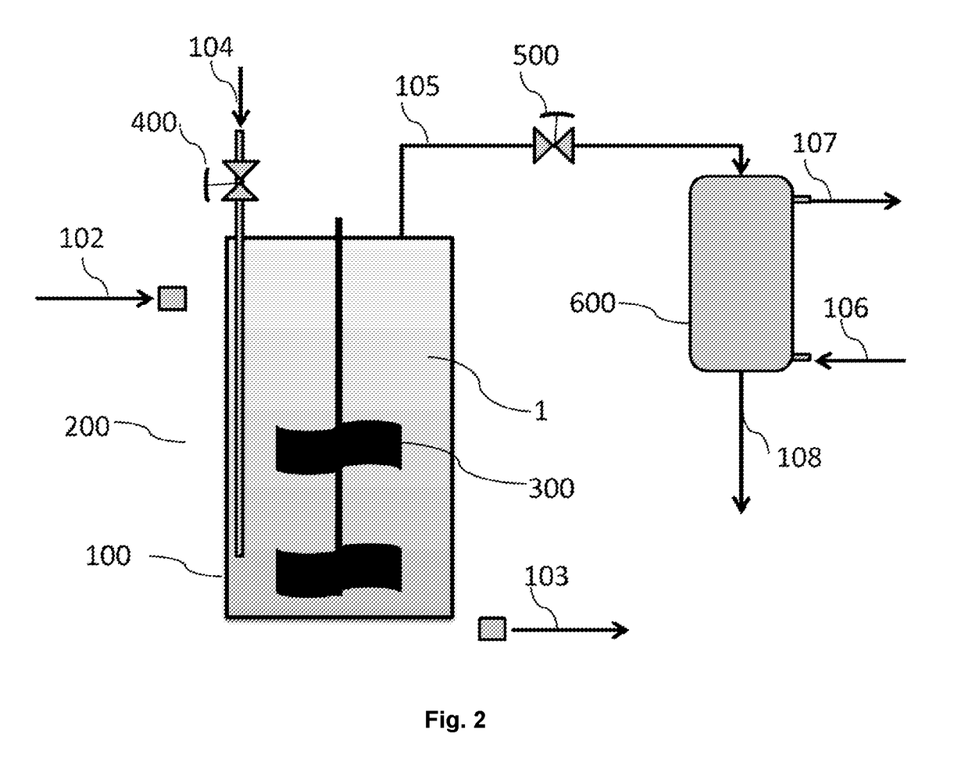
FIG. 2 illustrates a diagram of a reactor employed during furfural production according to the process described herein.

As seen in FIG. 2, a reactor 100 is used during furfural production. The prehydrolysate 1 is first placed in the reactor 100. Steam 102 is fed to a jacket 200 to heat the solution to the desired temperature. The exhausted steam 103 exits from the bottom. The solution is continuously agitated using a mixer 300. At the desired temperature, sulfuric acid 104 is added through a valve 400 to the bottom of the reactor 100. After 1-2 minutes, the valve 500 is opened to allow the furfural 105 to exit the reactor. The furfural stream is cooled down in a heat exchanger 600 by passing cold water 106. Hot/warm water 107 is collected at the other end of the heat exchanger. The furfural stream 108 is sent for further purification and concentration (e.g., using distillation).

It is described herein the production of value-added products from a prehydrolysate stream. The prehydrolysate stream is generally obtained by contacting biomass or wood chips with steam, hot water, a mild acidic stream, an alkaline solution, or solvents. This step is generally performed prior to pulping to extract hemicelluloses.

It is the object of the process described herein to provide a mean to recover efficiently valuable components such as lignin, sugars, and acetic acid from the prehydrolysate. It is a further objective of the process described herein to convert sugars to furfural at high yield.

The yield of furfural following the process encompassed herein is produced at a total molar yield of at least 70%.

The hemi-cellulosic feedstock solution comprising a total quantity of C5 sugars include but are not limited to hydrolyzed hardwood chips, hardwood (HW) lignin plant filtrate; black liquor from HW pulp mills; red liquor from hardwood sulfite pulp mills; C5 sugar streams from thermo-mechanical pulping bio-plants; waste streams of C5 sugars from cellulose nanocrystal (CNC) plants; and non-wood sources, such as oats and annual plants.

Figure 3:
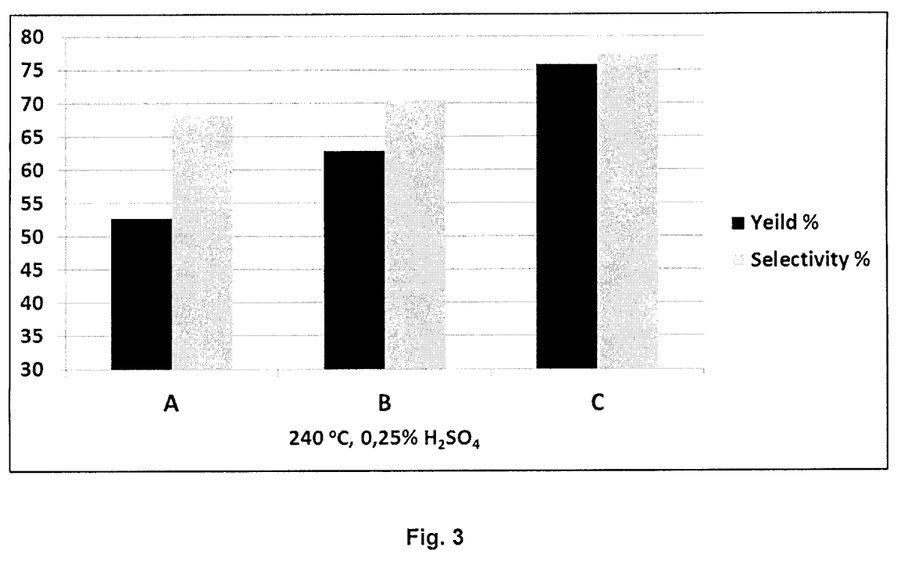
FIG. 3 illustrates the effect on the yield and selectivity of recovery of furfural after adding a sufficient quantity of concentrated sulfuric acid to obtain a 0.25 wt % reactor solution in $H_2SO_4$ initially in the solution, furfural remaining in the reaction mixture and not withdrawn from the reactor (A); acid added before heating the solution to 240° C. while the furfural was removed as it was produced (B); or acid added at a later stage when the feedstock solution reaches the desired temperature (240° C.) as encompassed in an embodiment described herein (C).

Accordingly, feedstock solution is placed in a closed stirred tank reactor. The major constituents of the prehydrolysate solution as produced from hardwood chips are presented in Table 1. The concentration of the major species can vary depending on the prehydrolysis conditions. The feedstock solution is heated to at least about 200° C., preferably at about 240° C., where between 220° C. and 240° C. is a preferred temperature range. Once the desired temperature is reached then the solution is acidified with a mineral acid. In a preferred embodiment the acid is dilute $H_2SO_4$. The acid reacts with the C5 sugars present to produce furfural from the C5 sugars. Contrary to known processes where the mineral acids are introduced from the beginning, before heating for example, by introducing the acid only when the desired temperature of the sugar solution is reached as described herein, side reactions are avoided and thus the yield of recovering is higher. As seen in FIG. 3 wherein the furfural yield and selectivity at three different conditions was measured (when acid initially present in the solution and no furfural removal, acid initially present in the solution and furfural was removed with the vapor, and acid was added at the target temperature and furfural was then immediately removed) adding the acid (0.25 wt % $H_2SO_4$ with respect to the solution weight) at a later stage when the feedstock solution reaches the desired temperature (240° C.), the yield and selectivity of recovery of furfural is increased.

TABLE 1

Major constituents of the prehydrolysate solution as produced from hardwood chips using hot water hydrolysis.

| Constituent | Value |
| --- | --- |
| Phenol, g/L | 2.1 |
| Furfural, g/L | 0.6 |
| HMF, g/L | 0.1 |
| Total Solid, % (w/w) | 4.25 |
| Total lignin, g/L | 7.6 |
| Acetic acid, g/L | 3.4 |
| Formic acid, g/l | 0.5 |
| Total sugars, g/L | 29.2 |
| Total C5 sugars, g/L | 24.4 |
| Xylose, g/L | 23.8 |
| pH | 3.5 |

The yield described in FIG. 3 when the acid was added to the prehydrolysate before heating the solution to the target temperature of 240° C. and no furfural was withdrawn from the reactor was about 52.7% (A). When the acid was added before heating the solution to 240° C. while the furfural was removed as it was produced, the yield was increased to about 62.8% (B). Most advantageously, when the sulfuric acid was added only when the solution temperature reached 240° C. and the furfural was removed as it was produced, the furfural yield increased to 75.7% (C). Thus compared to conventional operation in a batch reactor, the present approach can improve the yield from 52.7 to 75.7%.

Low acid dosage is needed in the disclosed process. In the described approach, the acid added needs to be only 0.1-0.5 wt % of the hydrolysate mass. This corresponds to about 0.07 kg to 0.36 Kg of sulfuric acid per kg of furfural produced. Much higher acid levels have been reported in the known processes. Values ranging from about 0.32 kg to 3 kg of sulfuric acid per kg of produced furfural were documented in literature. High charges of acid are needed when the feedstock is solid biomass which requires more time for digestion (to hydrolyze pentosane to pentose). In such cases, the furfural production process takes longer time (i.e., hours) compared to 2-3 minutes needed in the present invention.

Shortly after the introduction of the acid (1-2 min) the vapor phase begins to be released by opening a valve for example attached to the reactor to remove the furfural as it forms. The literature refers to the use of an organic phase to extract the furfural as it is produced. However, this option is complicated and expensive as the solvent has to be recovered and purified for further use.

The present process has the advantage that the furfural produced leaves the solution with the vapor. The vapor including water vapor and acetic acid is withdrawn from the reactor and is condensed and then further distilled to separate the furfural from water and acetic acid that are also present in the condensed vapor leaving the reactor. The process produces a high molar yield for furfural production of at least 70%. Accordingly, the use of sulfuric acid as exemplified herein provided a high furfural yield compared to conventional yields using xylose solutions and other acids which are typically around 50%.

In an embodiment, acetic acid is recovered using a hollow fiber contactor technology.

Total furfural yield is defined as the percentage of moles of furfural produced/total moles of C5 sugars initially present in the hemi-cellulosic biomass solution.

The furfural yield %, is more preferably at least 75% and even more preferably at least 80%, and most preferably at least 85%.

After production and removal of furfural, the organics are left in the reactor after being concentrated by a factor of 3-7. The organics (mostly polyphenolics) can be recycled to the mill recovery cycle or can be used in any one of several potential applications (e.g., replacement of phenol formaldehyde in wood adhesives).

Biomass hydrolysis with steam, hot water, or chemicals generates a solution rich in sugars, lignin and other valuable chemicals. Extracting some of these components can help increase revenues and generate new bio-products. Valorization of such a stream can be achieved by extracting lignin, acetic acid, and producing value-added products such as furfural from the sugars. A significant amount of lignin in the prehydrolysate can be obtained during the production of dissolving pulp. The extracted lignin has different characteristics compared to kraft lignin and is suitable for some niche applications. The remaining filtrate from lignin recovery is rich in sugars and can be converted by a novel approach to produce furfural whenever the wood furnish is composed of hardwood species. The furfural yield can be as high as 75.7%. Literature indicated that the removal of lignin in a first step enhances the furfural yield.

In known processes of extraction of furfural from biomass, there is no mention of lignin recovery from the prehydrolysate stream of dissolving pulp mills. In other processes, the lignin is considered as an impurity and a fermentation inhibitor during the fermentation of the sugars to produce various high value products (i.e. butanol, lactic acid, etc.). For example, it was suggested in the literature to remove lignin from kraft prehydrolysate by flocculating it with polyethylene oxide (PEO).

In another approach, the addition of a surfactant and calcium oxide have been proposed and tried to remove the lignin from a kraft-based dissolving pulp prehydrolysate. It is further proposed here that the calcium oxide be burned with the lignin to provide a source of energy to the lime kiln. No attempt was made to recover and valorize the prehydrolysate lignin.

Analysis of a prehydrolysate sample revealed that about 20% of the initial lignin in wood chips can be extracted in this stream when hardwood chips were employed. This lignin is quite different from kraft lignin as it has not been in contact with chemicals and contains no odorous sulfur species. The quality of the recovered lignin in the present process is different from kraft lignin (much lower molecular weight and odor-free). Thus, the lignin extracted can be used in place of phenol formaldehyde in wood adhesives at higher substitution levels.

Lignin from this prehydrolysate was extracted by concentrating the percent solids in the liquor from about 4% to 16% using a 1000 Da cut-off membrane. During this step, most of the lignin has been retained. Several membranes were evaluated and the 1000 Da cut-off membrane was selected since it gave the optimum lignin and sugar recovery. The solids concentration in the concentrate stream was about 16% solids. Thus, a concentration factor of about 5 (with respect to volume) was reached. A solids content of about 25-30% in black liquor solutions is desired for lignin precipitation. The concentrated stream was first acidified to pH=2 (from about pH=3.5), left for about 1 to 3 hours to coagulate with constant slow stirring, and, then, the lignin slurry was filtered to separate the lignin. The precipitated lignin had a much lower molecular weight compared to kraft lignin and should be suitable for several applications using this approach. It is possible to recover as much as 50% of the lignin present in the prehydrolysate. Concentrating the prehydrolysate by evaporation prior to lignin recovery was found to have a negative impact on lignin extraction and properties. It seems that further polymerization took place during evaporation which led to poor lignin filterability. It was previously found that the lignin content of the prehydrolysate affects negatively the conversion of sugars to other biochemicals. In previous studies, lignin and phenolics were removed using activated carbon before converting sugars to other biochemicals since these species act as fermentation inhibitors during the conversion process. However, such an approach will not allow subsequent recovery and use of the lignin.

The extracted sugars can be converted to a range of products such as xylitol, butanol, arabinitol, 1,3 propanediol, lactic acid and furfural. Contrary to existing processes that convert C5 sugars to furfural, which have a yield of only about 50%, it is disclosed herein that lower acid charges, injecting the acid only when the desired operating temperature is reached, and removing the furfural as it is formed were found to improve the furfural yield. The process described herein avoids high concentrations of furfural and acid in solution and long contact time with the catalyst (i.e., sulfuric acid) which lead to side reactions and lower the selectivity towards furfural formation. In particular, the optimum temperature to produce furfural was about 220-240° C. using about 0.25%-0 wt % sulfuric acid (based on prehydrolysate weight). At these conditions, the furfural yield was as high as 77% which is significantly higher than what has been reported in the present commercial plants.

The acetic acid present in the prehydrolysate ends up in the permeate of the ultrafiltration step used for the removal of lignin from prehydrolysate. Acetic acid can be removed from this stream using a hollow fiber contactor. In this case, a sodium hydroxide solution flowing in the lumen side and the prehydrolysate permeate flowing on the shell side was employed. Acetic acid diffused through the membrane and accumulated in the alkaline solution as sodium acetate. In a laboratory trial, about 97.6% of the acetic acid was recovered as sodium acetate and concentrated in the sodium hydroxide solution.

Some of the byproduct streams from the production of cellulose nanocrystals (CNC) using hardwood pulp or dissolving pulp are rich in xylose and sulfuric acid. The xylose (and other sugars) has to be removed before recycling the acid to the CNC plant to avoid caramelization of the sugars during the acid concentration step. One way to reduce the sugar content is to produce furfural from the C5 sugars as described above. The furfural can be removed as it is produced and the acid will be concentrated in the reactor. Further concentration may be needed as the CNC production requires generally 60 to 70% by weight acid. By doing so, another value-added product is produced along with the CNC.

The prehydrolysate from hardwood chips is rich in lignin, hemicelluloses, and acetic acid. Other components that may be present include formic acid, furfural and HMF. Recovering all the components present in the prehydrolysate may not be justified economically. However, recovery of the major constituents may present an excellent opportunity for pulp mills looking to diversify their product portfolio and to increase their revenue. After analysis of a hot water prehydrolysate from a hardwood kraft dissolving pulp mill producing about 550 t/d of dissolving pulp, it was found that this stream may contain about 83 t/d of sugars, 46 t/d of lignin, and 15 t/d of acetic acid. Extracting the lignin, the acetic acid and converting the sugars to furfural, using the process described herein, can lead to a significant increase in pulp mill revenues. In addition, the extraction of the prehydrolysate would allow the mill to increase pulp production by about 40 t/d.

Figure 4:
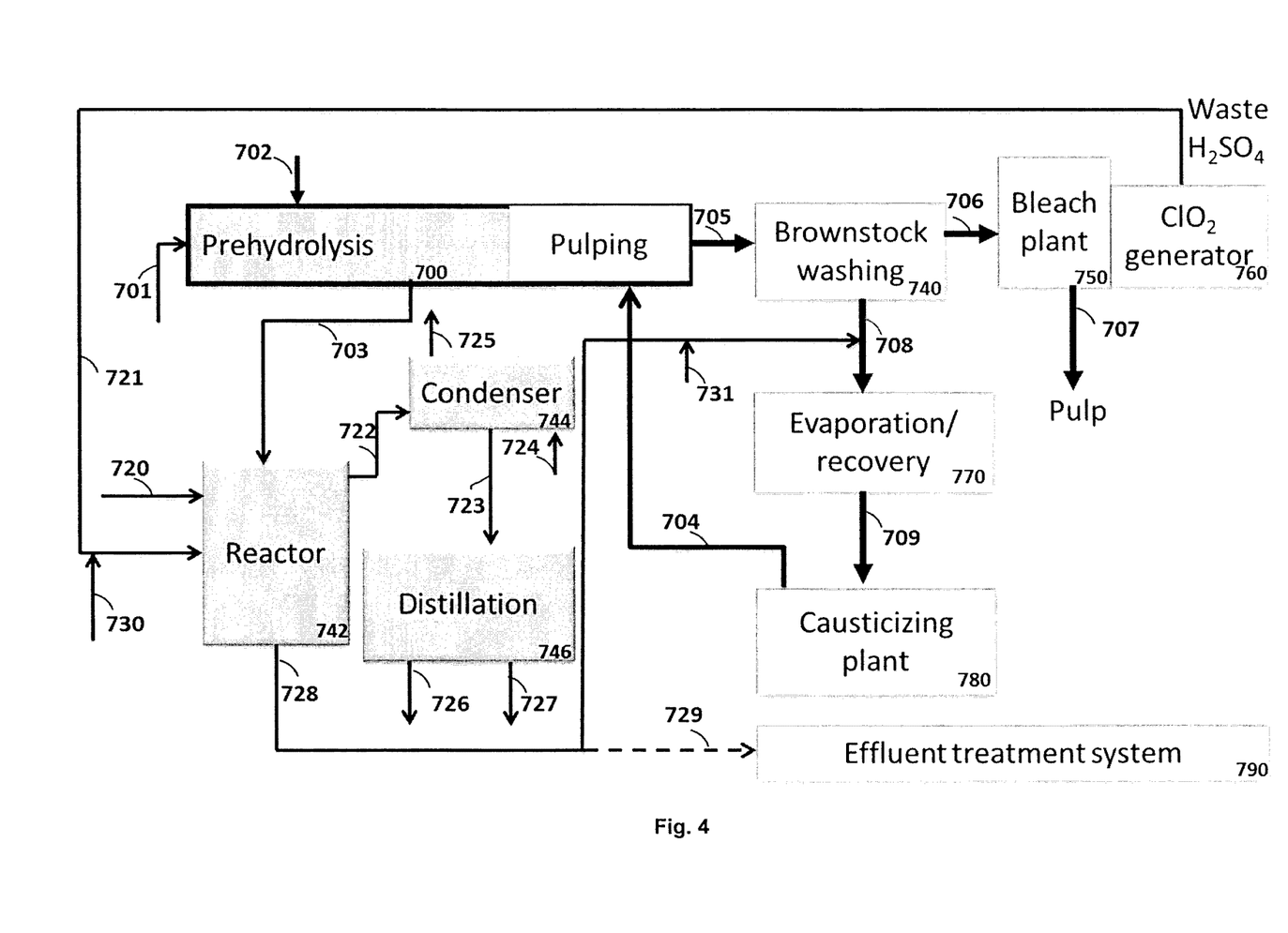
FIG. 4 illustrates how the furfural production process can be integrated in a kraft dissolving pulp mill.

FIG. 4 shows how the furfural production process can be integrated in a kraft dissolving pulp mill. In such a pulp mill, hardwood chips 701 are introduced to the digester 700. Steam or hot water (for heating) 702 is employed to perform the prehydrolysis step to release the sugars. The prehydrolysate is displaced from the digester 703 and white liquor 704 is introduced in the digester 700 for the pulping step. The pulp 705 is sent to the brownstock washing compartment 740. The washed pulp 706 is sent to the bleach plant 750 and chlorine dioxide produced in the $ClO_2$ generator 760 is employed in pulp bleaching. Bleached pulp 707 is produced. The residual pulping liquor 708 is sent to the evaporation and recovery compartment 770 to be concentrated and burned. Smelt from the recovery furnace is dissolved to obtain green liquor 709 which is sent to the causticizing plant 780 to produce white liquor 704 for cooking. The prehydrolysate 703 rich in C5 sugars is produced at about 170° C. and is sent to the furfural reactor 742 where it is further heated using steam 720, for example, to the desired temperature (200-240° C.). At the desired temperature, sulfuric acid 721 from the chlorine dioxide generator can be employed and added to the reactor 742. Part or all the spent acid from the generator is generally added to the recovery cycle (to black liquor) to maintain the sodium/sulfur balance in the liquor cycle. About 2-3 minutes after the addition of the acid, the vapor with the furfural produced 722 is released from the reactor to the condenser 744. In the condenser, warm or cold water (or any other mill stream to be heated) 724 is used to condense the vapor and obtain a furfural stream 723 rich in furfural and acetic acid. Hot water (or other hot stream) 725 is obtained and can be used in other compartments of the pulp mill. The aqueous furfural stream 723 is sent to distillation 746 to produce pure furfural 726 and concentrated acetic acid 727. The organics and the spent sulfuric acid 728 are released from the bottom of the reactor and sent to the recovery area where the organics will be concentrated and burned to produce energy. Part of the organics/spent acid stream 729 can be sent to the effluent treatment system 790 if necessary. Make-up sulfuric acid 730 may be added if spent acid from the chlorine dioxide generator is not sufficient for the furfural production. In such case, make up sodium hydroxide 731 is needed to maintain the Na/S balance. The spent acid from the $ClO_2$ generator 760 contains sodium sulphate, however, the latter has no effect on the furfural yield as observed in our laboratory. Any waste liquor stream from the pulp making process or the furfural plant can be sent to the effluent treatment system 790.

Compared to a stand-alone furfural plant the integration of the furfural plant in a pulp mill will lead to several benefits. These benefits include savings in energy consumption and chemical usage thereby reducing the cost of furfural production. Any waste generated can be handled in the mill's effluent treatment system. If desired, the lignin extraction step can be performed on stream 703 as described earlier in the present invention. The integration of the described furfural process is not limited to kraft dissolving pulp mills but it can be performed to any pulp mill where a C5-rich sugar stream is available for furfural production.

Example 1

A prehydrolysate solution containing about 7.6 g/L of total lignin was passed through a 1000 MW cut-off membrane and concentrated by a factor of 5. The total solids content in this case was about 16%. The concentrate of this step was acidified to pH=2 by adding sulfuric acid. The solution was left to coagulate for about 90 minutes at about 73° C. and then was filtered to recover the lignin. About 45% of the original lignin was recovered. The lignin content was about 91% of the total solids of the cake. The molecular weight distributions (Mw and Mn) of lignin from hardwood (and softwood) black liquor and of lignin from the prehydrolysate as measured by GPC with on-line multi-angle laser light scattering (MALLS) and UV detectors are presented in Table 2 for comparison purposes. Lignin extracted from the prehydrolysate has a lower weight average molecular weight (Mw) and number average molecular weight (Mn) and lower polydispersity (Mw/Mn ratio). The latter is a measure of the tightness of the molecular weight distribution.

TABLE 2

Molecular weight distribution of lignin obtained from hardwood (and softwood) black liquor of a kraft pulp mill and lignin from prehydrolysate (hardwood)

|  | MALLS | | UV | |
| --- | --- | --- | --- | --- |
|  | Mw (Da) | Mw/Mn | Mw (Da) | Mw/Mn |
| Lignin from prehydrolysate | 2810 | 1.15 | 1560 | 1.70 |
| Lignin from hardwood black liquor | 6300-9500 | 1.53-2.21 | 2420-3940 | 2.31-3.14 |
| Lignin from softwood black liquor | 12000-18000 | 1.65-2.47 | 5615-8020 | 2.85-4.37 |

Example 2

A synthetic sugar solution of 1 L containing about 22.5 g/L of xylose was prepared. The solution was heated to 240° C. in a set-up as shown in FIG. 2. At 240° C., 0.25 wt % sulfuric acid was added. After about 1-2 minutes, the vapor in the reactor was slowly released to collect the furfural solution. The furfural yield was 60% in this case. The same trial was repeated by adding about 8.3 g/L of kraft lignin to the xylose solution to determine the effect of lignin alone on the yield. The lignin was partially dissolved in the liquor. Furfural was produced as described above using the same apparatus. In this trial, the furfural yield dropped to 53% indicating that lignin has a negative effect on furfural yield.

TABLE 3

Effect of lignin content on furfural production from a synthetic prehydrolysate solution

|  | Xylose, g/L | Lignin, g/L | Furfural yield, % |
| --- | --- | --- | --- |
| Synthetic solution with no lignin | 22.5 | 0 | 60 |
| Synthetic solution with kraft lignin added | 23.0 | 8.3 | 53 |

Example 3

The effect of temperature and the amount of sulfuric acid added in furfural production is illustrated in the following example. A prehydrolysate solution of about 1 L containing about 22-24 g/L of xylose was employed. The acid was added when the target temperature was reached. After 1-2 minutes, the vapor was released and condensed to collect the furfural solution. The furfural solution had a volume of about 0.8 L. The furfural yield was the highest at 240° C. when 0.25 wt % sulfuric acid was added. Table 4 presents the furfural yield under the described conditions.

TABLE 4

Effect of temperature and amount of sulfuric acid added on the furfural yield.

| Temperature, ° C. | Sulfuric acid added at temperature | Furfural yield, % |
|---|---|---|
| 220 | 0.25% | 64.5 |
|  | 0.35% | 74.7 |
|  | 0.50% | 75.0 |
| 240 | 0.25% | 76.0 |
|  | 0.35% | 75.7 |
|  | 0.50% | 73.7 |
| 260 | 0.25% | 66.9 |
|  | 0.35% | 58.6 |
|  | 0.50% | 54.8 |

Example 4

This example illustrates the effect of sugar concentration on the furfural yield. The original prehyodlysate solution (xylose content: 22.8 g/L), a prehydrolysate solution diluted twice with water (xylose content: 12.12 g/L), and a prehydrolysate solution concentrated twice using a membrane system (xylose content: 46.2 g/L) were employed. The original prehydrolysate had the same composition as described in Table 1. Each solution was heated to 240° C. then about 0.36% sulfuric acid was added. The vapor was released to collect the furfural solution. Table 5 presents the measured yield in each case. The highest furfural yield was 76.0% obtained using the original prehydrolysate solution without diluting or concentrating.

TABLE 5

Furfural yield at various C5-sugar contents

| Prehydrolysate solution | Furfural yield |
|---|---|
| As produced | 76.0 |
| Diluted twice | 65.6 |
| Concentrated twice | 65.2 |

While the disclosure has been described with particular reference to the illustrated embodiments, it will be understood that numerous modifications thereto will appear to those skilled in the art. Accordingly, the above description and accompanying drawings should be taken as illustrative of the disclosure and not in a limiting sense.

While the disclosure has been described in connection with specific embodiments thereof, it will be understood that it is capable of further modifications and this application is intended to cover any variations, uses, or adaptations of the disclosure, within known or customary practice within the art and as may be applied to the essential features hereinbefore set forth, and as follows in the scope of the appended claims.

What is claimed is:

1. A method of producing furfural comprising:
   providing a hemi-cellulosic biomass solution comprising a total quantity of C5 sugars;
   heating the hemi-cellulosic biomass solution to a temperature of at least 200° C.;
   acidifying the hemi-cellulosic biomass solution with acid to produce furfural in vapor phase; and
   condensing the furfural to recover furfural in solution, wherein the furfural is produced at a total yield of at least 70% moles of furfural produced/the total moles of C5 sugars present in the initial hemi-cellulosic biomass solution.

2. The method of claim 1, wherein the total molar yield is at least 75%.

3. The method of claim 1, wherein the acid used to acidify the hemi-cellulosic biomass solution is sulfuric acid.

4. The method of claim 3, wherein the sulfuric acid has a concentration of 0.1%-0.5% w/w of the hemi-cellulosic biomass solution.

5. The method of claim 1, wherein the temperature to which the hemi-cellulosic biomass solution is heated is between 220° C.-240° C.

6. The method of claim 1, wherein the temperature to which the hemi-cellulosic biomass solution is heated is 240° C.

7. The method of claim 1, further comprising the step of purifying and concentrating the furfural by distillation.

8. The method of claim 1, wherein the furfural is separated from water and acetic acid by distillation.

9. The method of claim 1, wherein the hemi-cellulosic biomass solution is from hardwood chips, hardwood (HW) lignin plant; black liquor from HW pulp mills; red liquor from hardwood sulfite pulp mills; C5 sugar streams from thermo-mechanical pulping bio-plants; C5-rich sugar stream from cellulose nanocrystal (CNC) production; and non-wood sources.

10. The method of claim 9, wherein the non-wood sources are oats and annual plants.

11. The method of claim 1, wherein said hemi-cellulosic biomass solution is a prehydrolysate stream.

12. The method of claim 11, wherein said prehydrolysate stream is obtained by contacting the hemi-cellulosic biomass with steam, hot water, a mild acidic stream, an alkaline solution, or a solvent.

13. The method of claim 1, wherein the furfural is produced at a total molar yield of at least 75.7% moles of furfural produced/the total moles C5 sugars present in the initial hemi-cellulosic biomass solution.

14. The method of claim 1, wherein the furfural is produced at a total molar yield of at least 80% of moles of furfural produced/the total moles C5 sugars present in the initial hemi-cellulosic biomass solution.

15. The method of claim 1, wherein the furfural is produced at a total molar yield of at least 85% of moles of furfural produced/the total moles C5 sugars present in the initial hemi-cellulosic biomass solution.

16. The method of claim 1, further comprising a first step of extracting lignin from the provided hemi-cellulosic biomass solution by concentration using membranes.

17. The method of claim 16, wherein the membranes cut-off are 1000 Da.

18. The method of claim 17, wherein acetic acid is recovered from the permeate from the 1000 Da cut-off membranes using a hollow fiber contactor.

19. The method of claim 17, wherein the hemi-cellulosic biomass solution is acidified to pH 2 after being concentrated with the 1000 Da cut-off membranes.

* * * * *